(12) United States Patent
Richardson et al.

(10) Patent No.: US 10,989,699 B2
(45) Date of Patent: Apr. 27, 2021

(54) METHODS AND SYSTEMS FOR DETECTING AND QUANTIFYING PEROXY ACID AND PEROXIDE IN FLUIDS

(71) Applicant: CHEMTREAT, INC., Glen Allen, VA (US)

(72) Inventors: John Richardson, Hanover, VA (US); Mark Puchovich, Henrico, VA (US); Benjamin Niemaseck, Richmond, VA (US); Kevin White, Richmond, VA (US); James Wilkins, Midlothian, VA (US); Robert Bedinger, Richmond, VA (US)

(73) Assignee: CHEMTREAT, INC., Glen Allen, VA (US)

( * ) Notice: Subject to any disclaimer, the term of this patent is extended or adjusted under 35 U.S.C. 154(b) by 309 days.

(21) Appl. No.: 15/653,895

(22) Filed: Jul. 19, 2017

(65) Prior Publication Data

US 2018/0024103 A1    Jan. 25, 2018

Related U.S. Application Data

(60) Provisional application No. 62/364,033, filed on Jul. 19, 2016.

(51) Int. Cl.
| | | |
|---|---|---|
| *G01N 31/22* | (2006.01) | |
| *C12Q 1/30* | (2006.01) | |
| *B01L 3/00* | (2006.01) | |

(52) U.S. Cl.
CPC ............ *G01N 31/228* (2013.01); *B01L 3/502* (2013.01); *C12Q 1/30* (2013.01);
(Continued)

(58) Field of Classification Search
CPC ................ G01N 31/228; G01N 31/225; G01N 2333/908; C12Y 111/01006; B01L 3/502;
(Continued)

(56) References Cited

U.S. PATENT DOCUMENTS 6,332,951 B1    12/2001    Fladda et al.
6,432,661 B1 *   8/2002    Heitfeld ............... A01K 1/0152
                                                              435/192

(Continued)

FOREIGN PATENT DOCUMENTS

EP          0052834          6/1982

OTHER PUBLICATIONS

International Searching Authority,Notification of Transmittal of International Search Report and Written Opinion, dated Sep. 27, 2017, pp. 8.

(Continued)

*Primary Examiner* — Samuel P Siefke
(74) *Attorney, Agent, or Firm* — Oliff PLC

(57) ABSTRACT

Methods and systems are disclosed for analyzing and treating a fluid containing a peroxyacid and/or peroxide. A method of analyzing the fluid includes introducing into the fluid a decomposition agent that catalyzes decomposition of the peroxyacid and/or peroxide into decomposition products including oxygen, then directly or indirectly measuring an amount of oxygen produced after introduction of the decomposition agent, and determining an amount of the peroxyacid and/or peroxide present in the fluid. The amount of peroxyacid and/or peroxide in the fluid can also be monitored and controlled by further adjusting the amount of the peroxyacid and/or peroxide in the fluid based on the determined amount thereof. A system for performing the methods includes a decomposition agent infusion device for introducing the decomposition agent into a fluid sample, and a sensor for (Continued)

directly or indirectly measuring an amount of oxygen produced after introduction of the decomposition agent.

17 Claims, 7 Drawing Sheets

(52) U.S. Cl.
CPC .... *C12Y 111/01006* (2013.01); *G01N 31/225* (2013.01); *B01L 2200/16* (2013.01); *B01L 2300/0627* (2013.01); *G01N 2333/908* (2013.01)

(58) Field of Classification Search
CPC ......... B01L 2300/0627; B01L 2200/16; C12Q 1/30
See application file for complete search history.

(56) References Cited

U.S. PATENT DOCUMENTS

| | | | |
|---|---|---|---|
| 6,653,095 B1 | 11/2003 | Gwy et al. | |
| 2005/0112742 A1* | 5/2005 | Thompson | C12N 9/0065 435/168 |
| 2007/0238188 A1 | 10/2007 | Carr | |

OTHER PUBLICATIONS

Hurst et al., "Hydrogen Peroxide Oxidation by Chlorine Compounds. Reaction Dynamics and Singlet Oxygen Formation," Inorg. Chem. vol. 20, No. 8, pp. 2435-2438, 1981.

* cited by examiner

METHODS AND SYSTEMS FOR DETECTING AND QUANTIFYING PEROXY ACID AND PEROXIDE IN FLUIDS

This application claims the benefit of U.S. Provisional Application No. 62/364,033, filed Jul. 19, 2016, the contents of which are incorporated herein in their entirety.

TECHNICAL FIELD

This disclosure is directed to methods and systems for detecting and quantifying peroxyacid and peroxide in a fluid by introducing a decomposition agent into the fluid, and directly or indirectly measuring an amount of oxygen produced by a reaction between the decomposition agent and the peroxyacid and/or peroxide. The amount of oxygen produced after the addition of the decomposition agent can be correlated to the concentration of the peroxyacid and/or peroxide in the fluid. The concentration of the peroxyacid and/or peroxide in the fluid can then be adjusted by introducing a neutralizing agent into the fluid to neutralize the peroxyacid and/or peroxide, or adding more of the peroxyacid and/or peroxide into the fluid.

BACKGROUND

Peroxyacids, such as peracetic acid, are strong oxidizing agents that can be used as disinfectants in industrial systems, in particular as a sanitizer in food production plants. Peracetic acid can be used as an alternative to quaternary ammonium complexes to disinfect water streams because it is EPA approved and has a less detrimental effect on microbes in downstream waste processing. Peroxyacids are typically added to systems in a solution that contains peroxide.

Peracetic acid is a very corrosive substance. It can be challenging to measure amounts of peracetic acid in industrial systems because available methods often suffer from interferences. While on-line methods for measuring the amount of peracetic acid are generally less common, peracetic acid can be measured by collecting a sample and performing redox titration methods. Iodometry/iodimetry is one such class of titration method, where iodine can be used to quantify organic and inorganic substances, such as peracetic acid. Iodometric titrations can be difficult to implement on-line and can require amperometric titration.

Amperometric titration is a class of titration in which the equivalence point is determined through measurement of the electric current produced by the titration reaction. It can be challenging to accurately calibrate amperometric titrations in on-line systems. Colorimetric methods for measuring peracetic acid can also be used, but can be subject to interference from turbidity and color in water systems.

SUMMARY

This disclosure provides effective ways to determine the concentration of a peroxyacid, such as peracetic acid, and/or peroxide in a fluid. Specifically, in one aspect, it has been discovered that the amount of a peroxyacid or peroxide in a fluid can be determined by adding a decomposition agent to the fluid or a sample thereof, and then directly or indirectly measuring an amount of oxygen that is produced by a reaction between the decomposition agent and the peroxyacid and/or peroxide. The amount of oxygen produced after the addition of the decomposition agent can be correlated to the concentration of peroxyacid or peroxide in the fluid.

Determination of the amount of the peroxyacid and/or peroxide in the fluid can be used to control the amount of the peroxyacid and/or peroxide that is added to the fluid or to control an amount of a neutralizing agent added to the fluid to neutralize the peroxyacid and/or peroxide in the fluid.

In one embodiment, the disclosure provides a method of analyzing a fluid that includes at least one of peroxyacid or peroxide. The method includes introducing into the fluid a decomposition agent that catalyzes decomposition of the peroxyacid and/or peroxide into decomposition products including oxygen. Then, the method involves directly or indirectly measuring an amount of oxygen produced after the decomposition agent has been introduced, and determining an amount of the peroxyacid and/or peroxide present in the fluid based on the measured amount of oxygen produced.

Also provided herein is a method of monitoring and controlling an amount of peroxyacid and/or peroxide in a fluid. The method includes performing the above step of introducing into a sample of the fluid a decomposition agent that decomposes the peroxyacid and/or peroxide into decomposition products including oxygen, then directly or indirectly measuring an amount of oxygen produced after the introduction of the decomposition agent; and determining an amount of the peroxyacid and/or peroxide present in the fluid based on the measured amount of oxygen. The method also includes adjusting the amount of the peroxyacid and/or peroxide in the fluid based on the determined amount thereof.

The disclosure also provides a system for analyzing and treating a fluid containing at least one of peroxyacid or peroxide. The system includes a sample collector to collect a sample of fluid, a decomposition agent infusion device to introduce into the sample a decomposition agent that catalyzes decomposition of the peroxyacid and/or peroxide into decomposition products including oxygen, and a sensor to directly or indirectly measure an amount of oxygen produced after introduction of the decomposition agent.

DETAILED DESCRIPTION OF EMBODIMENTS

Figure 1:
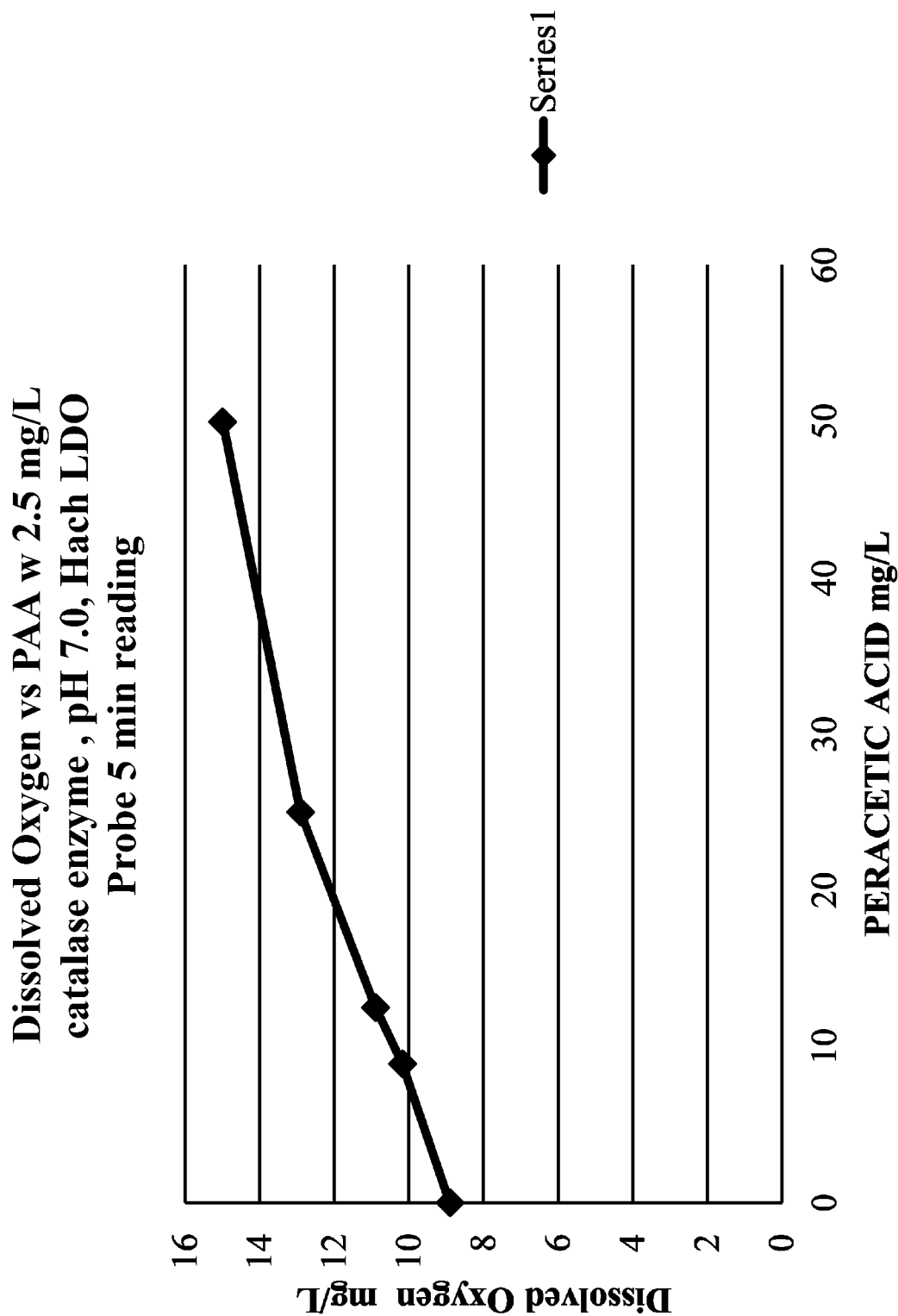
FIG. 1 is a graph showing the substantially linear relationship between dissolved oxygen concentration and peracetic acid concentration in the presence of a catalase enzyme.

This disclosure encompasses methods and systems for detecting and/or quantifying, as a target analyte, a peroxyacid, such as peracetic acid, and/or peroxide that is present in a fluid using a decomposition agent and measuring a change in an amount of oxygen produced in the fluid.

As discussed above, peroxyacids can be corrosive substances, and applying the methods and systems disclosed herein to quantify peroxyacid can provide valuable real-time information that can be used to control the amount that is added to a system, such as an industrial water system, to neutralize it, or to otherwise remove it from the system. It can also be useful to quantify the amount of peroxide in a fluid. Peroxyacids can include peracetic acid, performic acid, peroxymonosulfuric acid, peroxynitric acid, and metachloroperoxybenzoic acid.

Decomposition agents used to measure the concentration of peroxyacids or peroxide in a fluid can include any agent capable of decomposing peroxyacid and/or peroxide into decomposition products, including oxygen. Decomposition agents can include catalase enzyme, sodium hypochlorite (commonly known as bleach when dissolved in water), metal catalysts, alkaline solutions (such as sodium hydroxide), and haloamines. The decomposition agent can also be a physical process, such as irradiation with ultraviolet (UV light). As discussed in more detail below, catalase only catalyzes the decomposition of peroxide, but does not catalyze the decomposition of peroxyacid, whereas the remaining decomposition agents catalyze the decomposition of peroxyacid and peroxide.

Exemplary metal catalysts can include metals of Periods 4, 5, and 6 of the Periodic Table of Elements and the Lanthanide elements. Specifically, iron, copper, cobalt, chromium, manganese, platinum, zinc, gold, silver, nickel, palladium, osmium, molybdenum, vanadium, magnesium, cadmium, lead, selenium, polonium, ruthenium, rhodium, iridium, and mercury can be used as the decomposition agent. An exemplary metal catalyst is ferric chloride.

Haloamines can include one or more halogen atom associated with an amine group. Halogen atoms can include chlorine, fluorine, bromine, and iodine. Exemplary haloamines can include bromamine, chloramine, and iodoamine. Bromamine can include monobromamine or dibromaine. Chloramine can include monochloramine or dichloramine.

The decomposition agent can be added to the fluid or a sample thereof to decompose peroxyacid and/or peroxide into water and oxygen. For example, peracetic acid ($CH_3CO_3H$) is decomposed to acetic acid ($CH_3CO_2H$), hydrogen peroxide ($H_2O_2$), water ($H_2O$), and oxygen ($O_2$). $H_2O_2$ is further reduced to water ($H_2O$) and oxygen ($O_2$) as shown in the following reactions.

$$CH_3CO_3H + H_2O \rightleftharpoons CH_3CO_2H + H_2O_2$$

$$2CH_3CO_3H \rightleftharpoons 2CH_3CO_2H + O_2$$

$$2H_2O_2 \rightleftharpoons 2H_2O + O_2$$

The above three reactions go to the right in the presence of a decomposition agent. As discussed in more detail below, the amount of peroxyacid or peroxide can be determined by measuring the change in dissolved oxygen concentration after addition of the decomposition agent.

Catalase enzymes catalyze the decomposition of hydrogen peroxide to oxygen and water, as shown below:

$$2 H_2O_2 \xrightarrow{\text{catalase}} 2 H_2O + O_2$$

The catalase enzyme is a common enzyme found in nearly all living organisms exposed to oxygen, such as bacteria, plants, and animals. It can include any enzyme that catalyzes the decomposition of hydrogen peroxide to water and oxygen. Catalase enzymes can have a very high turnover number as compared to other enzymes. One catalase molecule can convert approximately 5 million molecules of hydrogen peroxide to water and oxygen each minute. Catalase enzymes are typically tetramers of four polypeptide chains, each over 500 amino acids long. Catalase enzymes can contain four porphyrin heme (iron) groups that allow the enzyme to react with the hydrogen peroxide.

Peroxyacids, such as peracetic acid, are in equilibrium with hydrogen peroxide in solution, as shown in the below equation.

$$H_2O_2 + CH_3CO_2H \rightleftharpoons CH_3CO_3H + H_2O$$

As catalase is specific to hydrogen peroxide decomposition, the addition of catalase to a sample containing peroxyacid and peroxide can result in a rapid increase in dissolved oxygen that corresponds to the concentration of hydrogen peroxide only. The equilibrium kinetics are relatively slow and thus addition of catalase will at least initially result in the decomposition of the peroxide component, but not the peroxyacid component. This allows the concentration of hydrogen peroxide to be determined independently from peroxyacids.

As indicated above, one or more of sodium hypochlorite, metal catalysts, alkaline solutions, haloamines, and UV light can similarly be used as decomposition agents to decompose peroxyacid and/or peroxide into decomposition components, including oxygen. The non-enzymatic decomposition agents can decompose both peroxyacid and peroxide such that the total concentration of peroxyacid and peroxide in the sample can be determined from the increase in the dissolved oxygen concentration. As discussed in more detail below, the concentration of the peroxyacid or peroxide can be determined from the increase in the dissolved oxygen concentration by using a standard curve.

Figure 2:
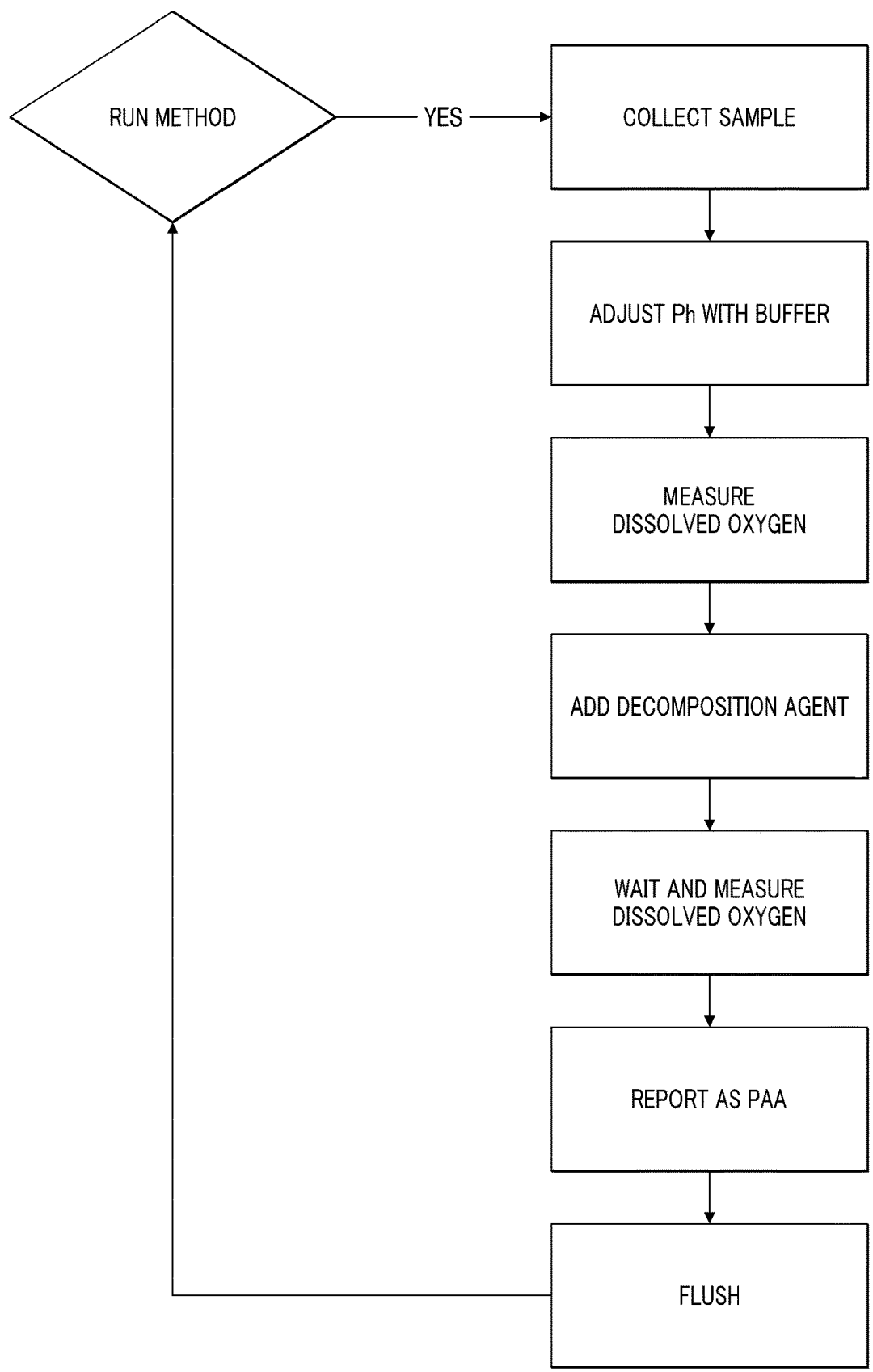
FIG. 2 is a flowchart illustrating an embodiment of a method for detecting and quantifying peracetic acid by adding a decomposition agent and measuring the amount of dissolved oxygen.

The methods described herein enable detection and quantification of a target peroxyacid or peroxide in a fluid by a quick and simple technique. FIG. 2 is a flowchart illustrating an exemplary method for detecting and quantifying peracetic acid by adding a decomposition agent and measuring the amount of dissolved oxygen.

In one aspect, as shown in the flowchart of FIG. 2, a fluid including a peroxyacid can be analyzed by collecting a sample of the fluid, introducing into the sample a decomposition agent, measuring an amount of oxygen in the sample, and determining an amount of the peroxyacid present in the sample based on the measured amount of dissolved oxygen. The method can also include adding a buffer to adjust the pH of the sample before adding the decomposition agent. The pH can be adjusted to a pH of about 6 to about 12, about 6.5 to about 11, about 7 to about 10, or about 7 to about 9.

The amount of dissolved oxygen in the sample can be measured before introducing the decomposition agent and after adjusting the pH. However, it may not be necessary to measure the amount of dissolved oxygen before introducing the decomposition agent if the amount of the dissolved oxygen in the fluid is known and relatively constant. The amount of dissolved oxygen in the sample before introducing the decomposition agent is typically less than about 10 mg/L. The dissolved oxygen concentration before addition of the decomposition agent can also be in a range of from about 0.1 to about 50 mg/L, about 1 to about 25 mg/L, about 1 to about 15 mg/L, about 1 to about 9 mg/L, or about 3 to about 7 mg/L. The maximum dissolved oxygen concentration in the sample can be recorded as discussed below.

The amount of dissolved oxygen produced in the sample can be measured one or more times after the decomposition agent has been added to the sample. The increase in the dissolved oxygen concentration in the sample can also be recorded. As discussed below, the dissolved oxygen concentration can be measured after the decomposition reaction is completed (i.e., the peroxyacid and/or peroxide is completely consumed) or the dissolved oxygen concentration can be measured at a predetermined time after the decomposition reaction begins, but before it is completed. For example, the dissolved oxygen concentration can be measured one or more times in a range of from about 5 seconds to an hour after the decomposition agent has been added to the sample to allow the decomposition reaction to be fully or partially carried out. For example, the measurement can be made about 10 seconds to 30 minutes, 20 seconds to 15 minutes, 30 seconds to 10 minutes, or 1 to 5 minutes after the decomposition agent has been added to the sample.

Measuring the amount of oxygen in the fluid or a sample thereof can be performed by any suitable method. The oxygen concentration can be directly or indirectly measured. For example, in one embodiment, an amount of oxygen produced by the reaction is directly measured by measuring a change in an amount of dissolved oxygen in the fluid after the introduction of the decomposition agent. The change in the amount of dissolved oxygen in the fluid is measured by directly measuring an amount of dissolved oxygen in the fluid after the introduction of the decomposition agent and comparing the measured amount of dissolved oxygen in the fluid to an amount of dissolved oxygen in the fluid before the decomposition agent was introduced. The amount of dissolved oxygen in the fluid before the decomposition agent is introduced may be known, or the method may further include directly measuring an amount of dissolved oxygen in the fluid before introducing the decomposition agent into the fluid. The dissolved oxygen concentration may be directly measured by a probe and/or sensor, such as an electrochemical sensor, including a galvanic sensor and polarographic sensor, or an optical oxygen sensor. The dissolved oxygen concentration may be measured in an open or closed system.

The amount of peroxyacids can be measured and distinguished from the amount of peroxide in a sample by taking advantage of the volatility of peroxyacids. Unlike peroxyacids, peroxide is not significantly volatile. Therefore, a liquid sample containing peroxyacid and peroxide can be treated such that peroxyacid is concentrated in gaseous form in a fluid that is substantially free of peroxide before introducing the decomposition agent into the fluid. The treatment may include purging a liquid sample containing peroxyacid and peroxide with air or an inert gas to transform the peroxyacid from a liquid phase to a gaseous phase. For example, the liquid sample may be purged with air or inert gas, such as nitrogen, carbon dioxide, or helium. The resultant fluid in the headspace can then be analyzed for an initial oxygen concentration. Then, decomposition of the peroxyacid in the headspace can be promoted by introducing the gaseous fluid in the headspace to a decomposition agent, such as UV light or a solid metal catalyst. Then, the resulting increase in oxygen concentration in the fluid in the headspace can be measured. The increase in oxygen concentration in the headspace will be proportional to only the volatile peroxyacid acid concentration because the fluid being analyzed in this embodiment is a gas that is substantially free of peroxide. As used herein, "fluid" can refer to a liquid or a gas. As used herein, "substantially free of peroxide" refers to an amount of peroxide less than 1 mg/L.

The volatile materials, including peroxyacid, in a liquid sample can also be captured via a purge-and-trap method. For example, a liquid sample containing peroxyacid and/or peroxide can be purged with air or an inert gas to transform the volatile materials including peroxyacid from the liquid phase to the gaseous phase. Then, the gaseous fluid can be swept into an analytical trap. The analytical trap can contain a solid sorbent to retain the volatile peroxyacid. The trapped peroxyacid can then be desorbed from the trap, a decomposition agent can be introduced, and the oxygen production can be measured to determine the amount of peroxyacid in the fluid, as discussed above.

In another embodiment, the amount of oxygen produced in the fluid may be indirectly measured, for example, by measuring an increase in pressure that results from the production of oxygen after the decomposition agent has introduced into the fluid sample in a closed system. The amount of peroxyacid and/or peroxide can be calculated from the change in pressure in the closed system, such as a pipe or other vessel, containing the fluid sample. In this case, the fluid sample containing peroxyacid and/or peroxide may be contained in a closed system connected to a pressure sensor. Any suitable sensor for measuring the pressure may be used. Upon introduction of the decomposition agent into the fluid sample, the decomposition agent reacts with the peroxyacid and/or peroxide to produce oxygen, causing the pressure in the system to increase. The increase in pressure can be measured by the pressure sensor, and the measured pressure increase can be correlated to the amount of peroxyacid and/or peroxide in the fluid without the need for probes to measure the dissolved oxygen levels. For example, the pressure may be measured before the decomposition agent is introduced into the fluid and after the decomposition agent has been introduced into the fluid. Alternatively, if the pressure of the system before introduction of the decomposition agent is known, then the pressure may only be measured after the decomposition agent has been introduced into the fluid. Then those values can be compared to determine the change in the pressure of the system after introduction of the decomposition agent. The change is pressure is proportional to the oxygen produced in the fluid due to the reaction between the decomposition agent and the peroxyacid and/or peroxide. This can then be correlated to the amount of peroxyacid and/or peroxide in the fluid.

The amount of dissolved oxygen in the sample after the decomposition of peroxyacid and/or peroxide is catalyzed by the decomposition agent can be in a range of from about 0.5 to about 100 mg/L, about 1 to about 75 mg/L, about 1 to about 60 mg/L, about 5 to about 20 mg/L, or about 5 to about 15 mg/L. After the addition of the decomposition agent to the sample, the amount of dissolved oxygen in the fluid can increase by a percentage in a range of from about 10 to about 100%, about 15 to about 80%, about 20 to about 70%, or about 30 to about 60%.

The increase in the amount of dissolved oxygen in the sample can be correlated to the amount of the peroxyacid, such as peracetic acid, and/or peroxide present in the sample. The amount of peroxyacid may be calculated, for example, by subtracting the initial dissolved oxygen concentration (i.e., before adding the decomposition agent) from the dissolved oxygen concentration measured after the addition of the decomposition agent to determine the increase in the dissolved oxygen concentration after the addition of the decomposition agent. Then, the peroxyacid concentration can be determined from the increase in the dissolved oxygen concentration by using a predetermined standard curve that compares the dissolved oxygen concentration to the concentration of peroxyacid.

A standard curve can be determined from the relationship between the increase in dissolved oxygen concentration and the concentration of peroxyacid so that the amount of the peroxyacid in the water system can be quantified. For example, to determine the standard curve, the increase in dissolved oxygen concentration can be measured in a fluid containing various known concentrations of the peroxyacid. The increase of dissolved oxygen concentration is then plotted against the known peroxyacid concentrations, and a regression of these data points is performed. The standard curve is preferentially based on a solution that has a similar equilibrium ratio between peroxyacid and peroxide as the peroxyacid solution that is added to the fluid as a disinfectant.

For example, FIG. 1 represents a standard curve. FIG. 1 shows a substantially linear relationship (with an $r^2$ value of about 0.97) between the dissolved oxygen concentration and the active peracetic acid concentration in the presence of a catalase enzyme. As discussed in more detail in Example 1, known amounts of a peracetic acid/hydrogen peroxide product having a 50:50 ratio of peracetic acid to hydrogen peroxide were added to fluid samples collected in a pipe. The x-axis numbers represent only the peracetic acid amounts in the samples. An initial concentration of dissolved oxygen in each sample was measured by a dissolved oxygen probe. Then, a catalase enzyme was added to each sample. After a period of time, the probe was used to measure the dissolved oxygen levels again. The increase in the dissolved oxygen levels was then plotted against the known peroxide concentrations for the samples, and a regression of these data points was performed to produce the standard curve shown in FIG. 1.

The graph in FIG. 1 shows that the amount of dissolved oxygen that is produced after the addition of the catalase enzyme (on the y-axis) is substantially proportional to the amount of active peracetic acid (on the x-axis) present in the samples. Because the catalase enzyme only breaks down hydrogen peroxide, the amount of dissolved oxygen that is produced will be directly proportional to the amount of hydrogen peroxide present in the sample.

Similarly, the peroxide concentration in a fluid can be determined from the increase in the dissolved oxygen concentration by using a predetermined standard curve that compares the dissolved oxygen concentration to the concentration of peroxide. A standard curve can be determined from the relationship between the increase in dissolved oxygen concentration and the concentration of peroxide so that the amount of peroxide in the water system can be quantified. The standard curve can be determined in the same manner as the standard curve for peroxyacid by measuring the increase in dissolved oxygen concentration in fluids containing various known concentrations of peroxide, plotting the increase of dissolved oxygen concentration against the known peroxide concentrations, and performing a regression of these data points.

As mentioned above, catalase only catalyzes the decomposition of peroxide, but does not catalyze the decomposition of peroxyacid, whereas the remaining decomposition agents catalyze the decomposition of peroxyacid and peroxide. In one aspect, catalase (or any of the other decomposition agents) can be used as the decomposition agent to determine the amount of peroxyacid or peroxide in a fluid by taking a sample of the fluid, measuring the increase in dissolved oxygen concentration, and correlating that to the amount of peroxyacid or peroxide using a predetermined standard curve, as discussed above. Assuming that the standard curve was based on a solution having a peroxyacid/peroxide equilibrium ratio that is the same or substantially similar to the solution being added to system of interest, the increase in dissolved oxygen measured in the system can reliably be correlated to the peroxyacid concentration, the peroxide concentration, or both.

In another aspect, two samples of the fluid can be taken. Catalase can be added to a first sample and a different decomposition agent, such as sodium hypochlorite, can be added to a second sample. Then, the increase in dissolved oxygen concentration can be measured in each sample. The concentration of peroxyacid can be determined by subtracting the increase in dissolved oxygen concentration in the first sample from the increase in the dissolved oxygen concentration in the second sample. In this regard, the increase in dissolved oxygen concentration in the first sample corresponds to the amount of peroxide in the sample as catalase only catalyzes the decomposition of peroxide and not peroxyacid. The increase in dissolved oxygen concentration in the second sample corresponds to the amount of peroxyacid and peroxide in the sample because the other decomposition agents, such as sodium hypochlorite, cause or catalyze the decomposition of both peroxyacid and peroxide. Therefore, the concentration of peroxyacid can be determined by subtracting the dissolved oxygen production in the first sample from that in the second sample to eliminate the dissolved oxygen production resulting from the decomposition of peroxide.

Figure 3:
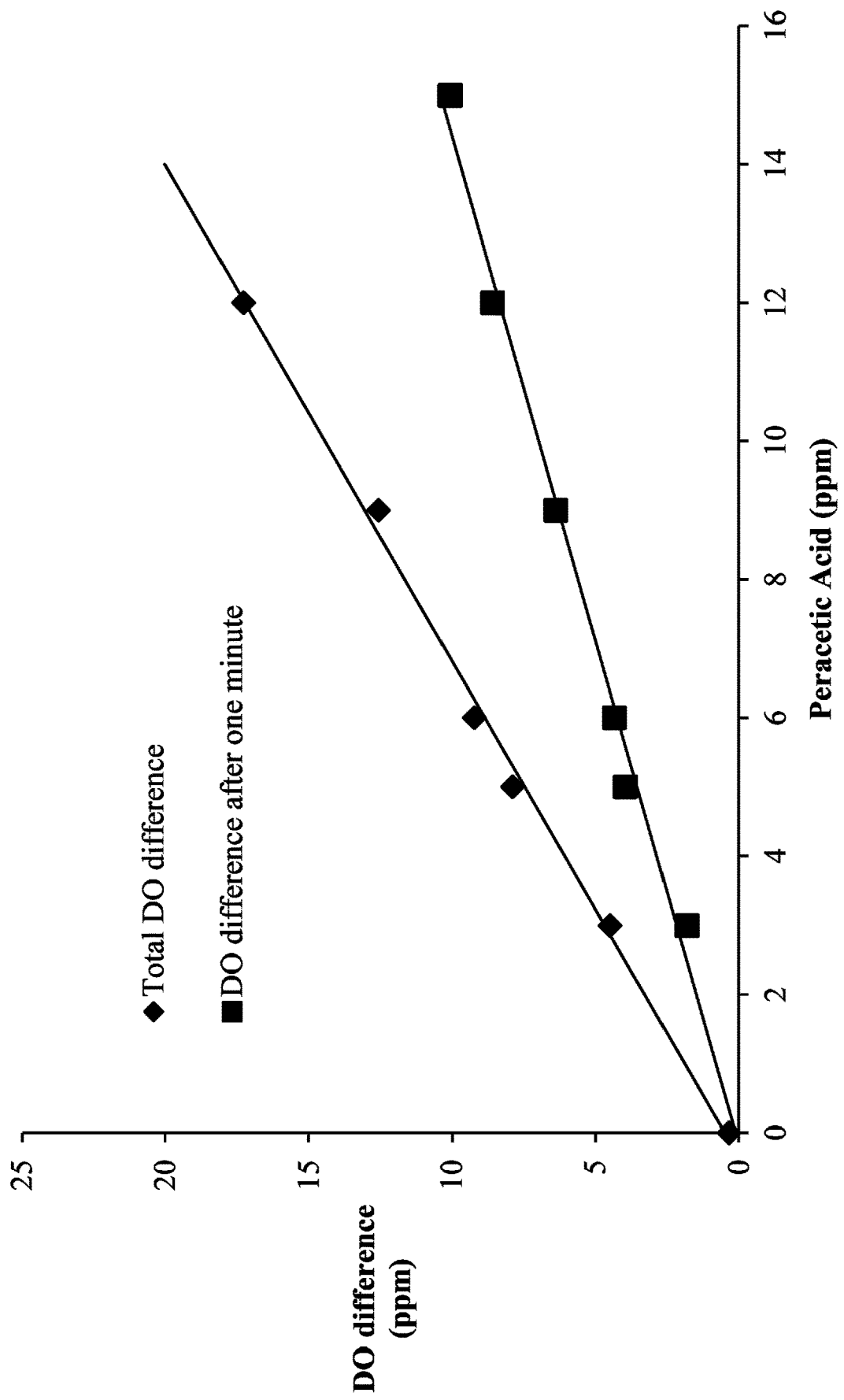
FIG. 3 is a graph showing the linear relationship between the dissolved oxygen concentration and the peracetic acid concentration in the presence of sodium hypochlorite (NaOCl) after peracetic acid is completely consumed and one minute into the decomposition reaction.

As discussed in more detail in Example 2, FIG. 3 shows a substantially linear relationship between the dissolved oxygen concentration and the peracetic acid concentration in the presence of sodium hypochlorite (NaOCl) one minute into the decomposition reaction and after completion of the decomposition reaction (i.e., after the peracetic acid is completely consumed). Samples with known amounts of peracetic acid were collected in a pipe. An initial concentration of dissolved oxygen in each sample was measured using a dissolved oxygen probe. Then, sodium hypochlorite was added to each sample. The dissolved oxygen probe was used to measure the dissolved oxygen levels at 1 minute after the addition of sodium hypochlorite and after completion of the decomposition reaction. As shown by the square points, the amount of dissolved oxygen that is produced one minute after the addition of the sodium hypochlorite (on the y-axis) is substantially proportional to the amount of peracetic acid (on the x-axis) present in the samples. As shown by the diamond points, the amount of dissolved oxygen that is produced after completion of the decomposition reaction (on the y-axis) is substantially proportional to the amount of peracetic acid (on the x-axis) present in the samples.

Therefore, the peroxyacid and/or peroxide concentration in a sample can be determined by measuring the dissolved oxygen concentration in the sample at a predetermined time after the decomposition agent is added and it is not necessary to wait for the decomposition reaction to be completed. The measured amount of dissolved oxygen can be correlated to the amount of peroxyacid or peroxide using a predetermined standard curve that compares the dissolved oxygen concentration to the concentration of peroxyacid or peroxide, which may be measured at the peak concentration of dissolved oxygen or at a predetermined time after the decomposition agent was added. For example, the dissolved oxygen concentration can be measured at 5 seconds, 10 seconds, 30 seconds, 1 minute, 2 minutes, 3 minutes, 5 minutes, 10 minutes, 20 minutes, 30 minutes, 45 minutes, or more after the decomposition agent was added to the sample. Then, the amount of peroxyacid and/or peroxide can be determined by using a standard curve that compares the dissolved oxygen concentration at the peak value or at the predetermined time to the peroxyacid and/or peroxide concentration.

Figure 4:
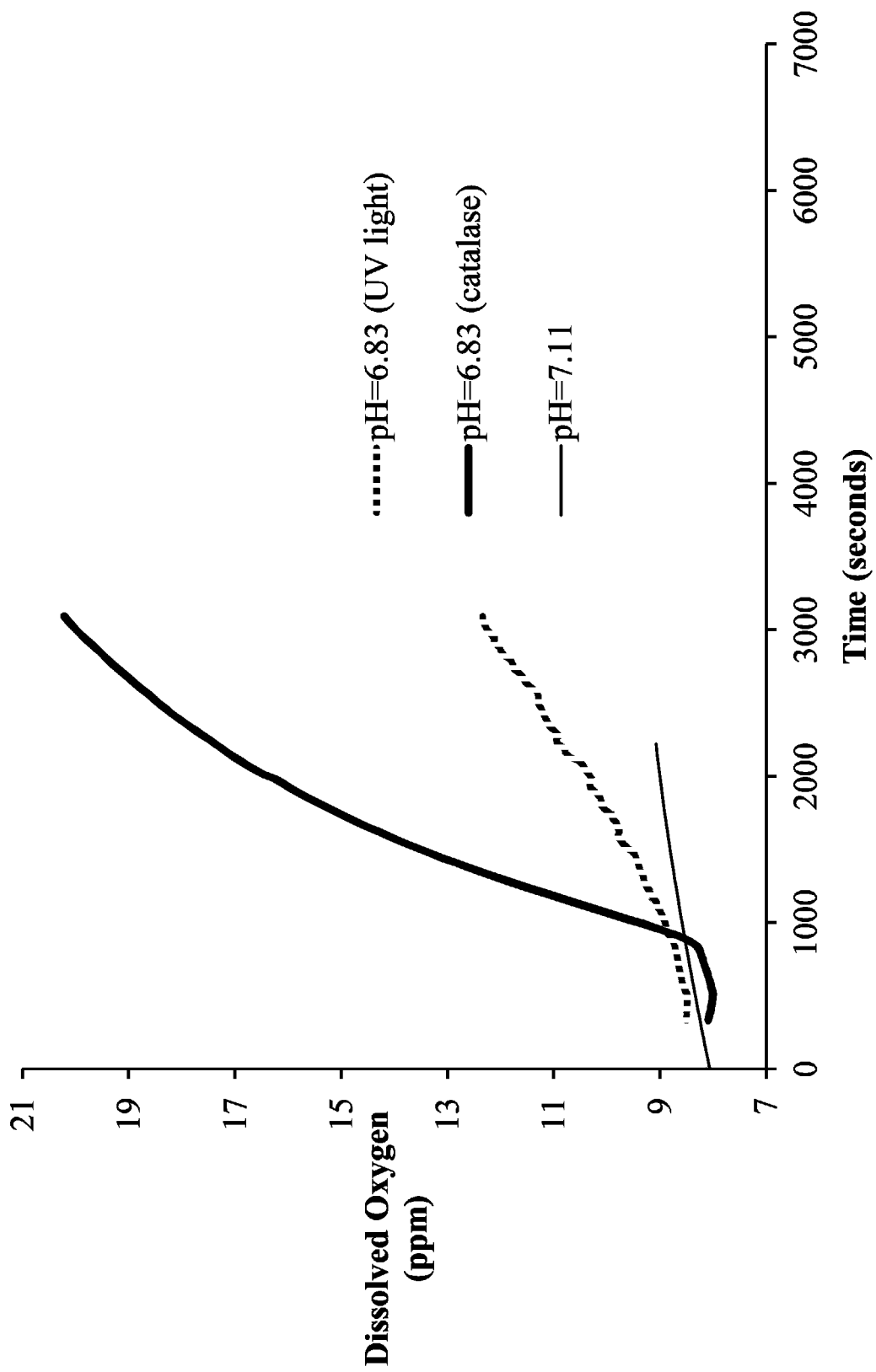
FIG. 4 is a graph showing the rates of dissolved oxygen production in three fluid samples containing peracetic acid: (1) in the presence of catalase as the decomposition agent; (2) in the presence of UV light as the decomposition agent; and (3) in the absence of a decomposition agent (i.e., the natural decomposition of peracetic acid).

As discussed in more detail in Example 3, FIG. 4 is a graph showing the rates of dissolved oxygen production in three fluid samples containing peracetic acid: (1) in the presence of catalase as the decomposition agent; (2) in the presence of UV light as the decomposition agent; and (3) in the absence of a decomposition agent at a pH of 7.11 (i.e., the natural decomposition of peracetic acid). As shown in FIG. 4, the dissolved oxygen concentration sharply increases starting about 900 seconds when the catalase enzyme was added in sample (1). There is also an increase in the dissolved oxygen concentration starting at about 900 seconds when UV light is irradiated into sample (2). However, the rate dissolved oxygen production when UV light is used as the decomposition agent in sample (2) is lower than that when catalase enzyme is used as the decomposition agent in sample (1). When no decomposition agent is used (at a pH of 7.11) in sample (3), the dissolved oxygen concentration increases linearly over time at a rate lower than that when catalase (sample (1)) and UV light (sample (2)) are used as the decomposition agents. The natural decomposition rate of peracetic acid is lower than that when catalase and UV light are used as the decomposition agents.

The amount of the decomposition agent to be added to the sample will vary depending on which decomposition agent is used and depending on the expected amount of peroxyacid and/or peroxide in the fluid. For example, the decomposition agent can be added to the sample in an amount in a range of from about 0.1 to about 100 mg/L, about 1 to about 50 mg/L, about 2 to about 25 mg/L, or about 2.5 to about 10 mg/L.

The decomposition agent may be introduced free floating into the sample or the decomposition agent may be immobilized on a surface that is in fluid communication with the sample in a way that allows the decomposition agent to interact with and decompose peroxyacid and/or peroxide. An immobilized decomposition agent may include a soluble decomposition agent that is attached to a substrate. The substrate may be any suitable substrate for attaching a decomposition agent. Examples of the substrate may include polyurethane foams, polyacrylamide gels, polyethylenemaleic anhydride gels, polystyrenemaleic anhydride gels, cellulose, nitrocellulose, silastic resins, porous glass, macroporous glass membranes, glass beads, activated clay, zeolites, alumina, silica, silicate, and other inorganic and organic substrates. The decomposition agent may be attached to the substrate via any suitable method including, for example, carrier covalent binding, cross-linking, physical adsorption, ionic binding, and entrapping.

When using any of the techniques described above, the target peroxyacid or peroxide can be present and detected in the sample in an amount in a range of, for example, from 0.05 ppm to 10,000 ppm, from 0.1 ppm to 1,000 ppm, from 0.5 ppm to 100 ppm, from 1 ppm to 80 ppm, or from 5 ppm to 50 ppm.

The methods described herein enable the target peroxyacid and/or peroxide analyte to be quantified by a quick and simple technique. This enables the assay to be performed to provide real-time information regarding analyte levels, which in turn can be used to control the amount of analyte that is added to the system, removed from the system, and/or neutralized.

In one embodiment, a neutralizing agent can be added to the fluid in a process system based on the determined amount of peroxyacid and/or peroxide to neutralize the peroxyacid and/or peroxide in the system to reduce the toxicity of waste streams in a downstream waste treatment unit. For example, if the concentration of peroxyacid and/or peroxide is too high, the peroxyacid and/or peroxide can inhibit or potentially kill beneficial microorganisms in a waste treatment unit downstream from the water system.

The neutralizing agent, for example, can be introduced in an amount sufficient to neutralize the peroxyacid and/or peroxide based on the determined amount thereof from measuring the maximum dissolved oxygen concentration. The neutralization can be achieved by adding neutralizing chemicals continuously into the process stream in amounts that are based on the detected amounts of peroxyacid and/or peroxide. Alternatively, the neutralizing chemicals can be added intermittently or only when the concentration of the peroxyacid and/or peroxide exceeds a predetermined threshold value.

Suitable neutralizing agents that can be added to the process stream to neutralize the peroxyacid and/or peroxide can include reducing agents, such as bisulfite, erythorbate, or cerium (III). Bisulfite can include sodium, potassium, and ammonium bisulfite salts, and sodium metabisulfite.

The addition of excess bisulfite can cause problems in a downstream waste treatment unit because bisulfite consumes or removes oxygen from the waste stream, which can kill beneficial microorganisms that treat the water and keep the biosystem healthy. An advantage of the methods and systems disclosed herein is that, by measuring a total peroxyacid and/or peroxide concentration, a sufficient amount of the reducing agent for neutralizing the peroxyacid and/or peroxide can be determined. Therefore, a sufficient amount of a reducing agent, such as bisulfite, can be added to the fluid and the addition of an excess amount of the reducing agent, which can cause problems in a downstream waste treatment unit, can be avoided.

In another aspect, the neutralizing agent can be a decomposition agent or catalyst, which neutralizes the peroxyacid and/or peroxide via a different chemistry than reducing agents. The decomposition agent or catalyst can be added to the fluid to decompose the peroxyacid and/or peroxide in the fluid. The decomposition agent or catalyst can include any of the decomposition agents discussed above, such as sodium hypochlorite, metal catalysts, alkaline solutions, haloamines, or UV light. Catalase can also be used as the neutralizing agent to decompose peroxide. However, as discussed above, catalase does not decompose peroxyacid.

Catalase, sodium hypochlorite, metal catalysts, alkaline solutions, haloamines, and UV light are advantageous neutralizing agents because, as indicated above in connection with their roles as decomposition agents, they add oxygen to the system when breaking down peroxyacid and/or peroxide, and the added oxygen can be beneficial for downstream waste treatment units.

However, oxygen production may not be desirable when the downstream biological system is anaerobic. In this regard, the addition of a decomposition agent or catalyst, such as ferric, for example, used as a coagulant, can interact with the peroxyacid to yield oxygen and upset conditions in a downstream anaerobic system. In this case, a reducing agent, such as bisulfite, which consumes oxygen, can be added to the fluid as the neutralizing agent to neutralize the peroxyacid and/or peroxide, and avoid the production of oxygen that may disrupt the downstream anaerobic system. Alternatively, a decomposition agent or catalyst, such as ferric, may be introduced into the fluid well upstream of the anaerobic system to allow time for the dissolved oxygen to dissipate before the addition of a reducing agent, such as bisulfite. A reducing agent, such as bisulfite, which consumes oxygen, can be added to the fluid downstream from the addition of the decomposition agent, which produces oxygen, but upstream of the anaerobic system. By separating the introduction of the decomposition agent from the introduction of the reducing agent, a low dissolved oxygen concentration can be obtained in the downstream anaerobic system.

Even with an aerobic downstream system, if a significant excess amount of the decomposition agent or catalyst is added to the fluid over the amount necessary for decomposing the peroxyacid and/or peroxide, it can also kill beneficial microorganisms in the downstream waste treatment unit and damage the ecosystem. Similar to the reducing agents, the measuring techniques disclosed herein also permit a proportional amount of the decomposition agent or catalyst to be added to the fluid without harming the biological system.

In particular, the measuring techniques described herein advantageously enable the amount of the neutralizing agent (e.g., a reducing agent or a decomposition agent) to be more precisely calculated. In this regard, the amount of the neutralizing agent to be added to the fluid can be calculated from the measured concentration of the peroxyacid and/or peroxide in the sample. For example, the amount of the neutralizing agent to be added to the fluid can be determined based on the concentration of the peroxyacid and/or peroxide in the sample and the flow rate of the fluid through the water system. In one aspect, the amount of the neutralizing agent added to the fluid can be calibrated by using fluids with known amounts of peroxyacid and/or peroxide to standardize catalysis or neutralization activity.

Therefore, the neutralizing agent can be added in an amount sufficient to neutralize the peroxyacid and/or peroxide without adding excess neutralizing agent that may kill beneficial microorganisms in the waste treatment unit. In other words, by determining the amount of peroxyacid and/or peroxide in the fluid, the amount of the neutralizing agent, such as bleach, to be added to the system to neutralize the peroxyacid and/or peroxide can be precisely controlled such that excess bleach, which can kill beneficial microorganism in the waste treatment unit, is not added to the fluid.

The neutralization of peroxyacid and/or peroxide can also be accomplished by directing the process stream to fixed media that is sufficient to neutralize the target peroxyacid or peroxide. Based on the detected amount of the target peroxyacid or peroxide, a control loop can divert a portion or all of the process stream to a fixed media to neutralize the peroxyacid or peroxide. In one embodiment, the control loop can divert a portion or all of the process stream to the fixed media when the concentration of target peroxyacid or peroxide in the stream exceeds a predetermined threshold value. The fixed media may include the neutralizing agents such as bisulfite, erythorbate, cerium (III), ferric(III), catalase, sodium hypochlorite, metal catalysts, alkaline solutions, and haloamines. The fixed media can include immobilized rare earth elements or manganese dioxide. See, e.g., U.S. patent application Ser. No. 14/874,944, the disclosure of which is incorporated herein by reference in its entirety. Fixed media has an advantage that it produces fewer or no soluble reaction products that interfere with downstream processes.

In one method, the concentration of the peroxyacid and/or peroxide in the fluid is continuously monitored and controlled. For example, the method may involve measuring the oxygen concentration and/or pressure following (and/or immediately before) the addition of the neutralization agent to continuously monitor the concentration of peroxyacid and/or peroxide in the fluid, and making the appropriate adjustments to the concentration as needed. For example, the peroxyacid and/or peroxide concentration may be adjusted by introducing more peroxyacid/peroxide solution into the fluid to increase the concentration, or introducing a neutralization agent into the fluid to decrease the concentration, or directing the fluid to fixed media containing a neutralization agent to also decrease the concentration. Continuous monitoring enables the concentration of the peroxyacid and/or peroxide in the fluid to be controlled to be within a desired predetermined range.

For example, the method may include measuring the oxygen concentration or pressure, and introducing a predetermined amount of the decomposition agent into the fluid or a sample thereof automatically at predetermined intervals. For example, an initial oxygen concentration or pressure may be automatically measured every 5 minutes, 15 minutes, 30 minutes, hour, 2 hours, or any other suitable interval. Then, a predetermined amount of the decomposition agent may automatically be introduced into the fluid or a sample thereof. Then, after a predetermined period of time, the oxygen concentration or pressure may be automatically measured again to determine the change in the oxygen concentration or pressure for the purpose of calculating the peroxyacid and/or peroxide concentration. For example, the measured values may be compared to a predetermined standard curve for determining the peroxyacid and/or peroxide concentration. Then, the peroxyacid and/or peroxide concentrations may be adjusted as needed to be within a predetermined range based on the calculated peroxyacid and/or peroxide concentration in the fluid. For example, more peroxyacid/peroxide solution may be introduced into the fluid to increase the concentration, or a predetermined amount of a neutralization agent may be introduced into the fluid to decrease the concentration, or the fluid may be directed to fixed media containing a neutralization agent to decrease the concentration.

The pH of the fluid or any other measurable property may also be monitored and controlled to be within a desired range. For example, the pH may be controlled to be within any of the predetermined ranges discussed above, such as a range of about 6.5 to about 11. For example, the pH may also be continuously measured at predetermined time intervals. Those measurements may be compared to a predetermined pH range. If the measured pH is outside of the predetermined range, then a buffer may be introduced into the fluid for adjusting the pH of the fluid to be within the predetermined range. The pH may be continuously measured until the pH is determined to be within the predetermined range or until a predetermined time interval has passed.

A system for automatically performing the methods is also disclosed. The system may include a sample collector configured to collect a sample of fluid, a decomposition agent infusion device configured to introduce into the sample a decomposition agent that decomposes the peroxyacid and/or peroxide into decomposition products including oxygen, and a sensor configured to directly or indirectly measure an amount of oxygen produced by a reaction between the decomposition agent and the peroxyacid and/or peroxide.

The sample collector may be any suitable device for collecting a sample of the fluid. For example, the sample collector may be a pipe or other vessel for collecting a sample directly from a fluid. A portion of the fluid may be diverted into pipe or vessel for analysis. The sample collector may be an open or closed system.

The system may further include a controller that is configured to determine an amount of the peroxyacid and/or peroxide in the fluid based on the measured amount of oxygen produced by the reaction. The controller may also control an amount of peroxyacid and/or peroxide, or an amount of a neutralization agent that is introduced into the fluid based on the determined amount of the peroxyacid and/or peroxide in the fluid. The controller may be a processor, microprocessor, CPU, or any other suitable device for receiving, processing, analyzing, and recording information, including measurement results from the sensor and any other device, and transmitting instructions and/or command signals to other devices based on the received information.

The sensor may be an oxygen sensor that is configured to directly measure an amount of oxygen produced by the reaction, a pressure sensor that is configured to indirectly measure an amount of oxygen produced by the reaction by measuring a change in pressure in a closed system containing the sample after introduction of the decomposition agent into the sample, or any other suitable sensor or device for measuring an amount of oxygen produced after introduction of the decomposition agent. For example, the sensor can be a luminescent dissolved oxygen (LDO) probe or any other probe for measuring an amount of oxygen. The probe may have, for example, a sensor head that takes the measurement. The sensor could alternatively be an electrochemical sensor, including a galvanic sensor and polarographic sensor, or an optical oxygen sensor The decomposition agent infusion device can be configured to introduce any suitable decomposition agent into the fluid or sample thereof, including, for example, catalase enzyme, sodium hypochlorite (commonly known as bleach when dissolved in water), metal catalysts, alkaline solutions (such as sodium hydroxide), and haloamines. The decomposition agent infusion device 16 can also be configured to introduce a decomposition agent via a physical process, such as by irradiating the fluid or a sample thereof with ultraviolet (UV light).

The system may also include a neutralization agent infusion device configured to introduce a neutralization agent into the fluid, a buffer infusion device configured to introduce a buffer into the fluid or a sample thereof, a peroxyacid solution infusion device configured to introduce a peroxyacid solution into the fluid or a sample thereof, and any other infusion device for introducing any substance into the fluid or a sample thereof.

Figure 5:
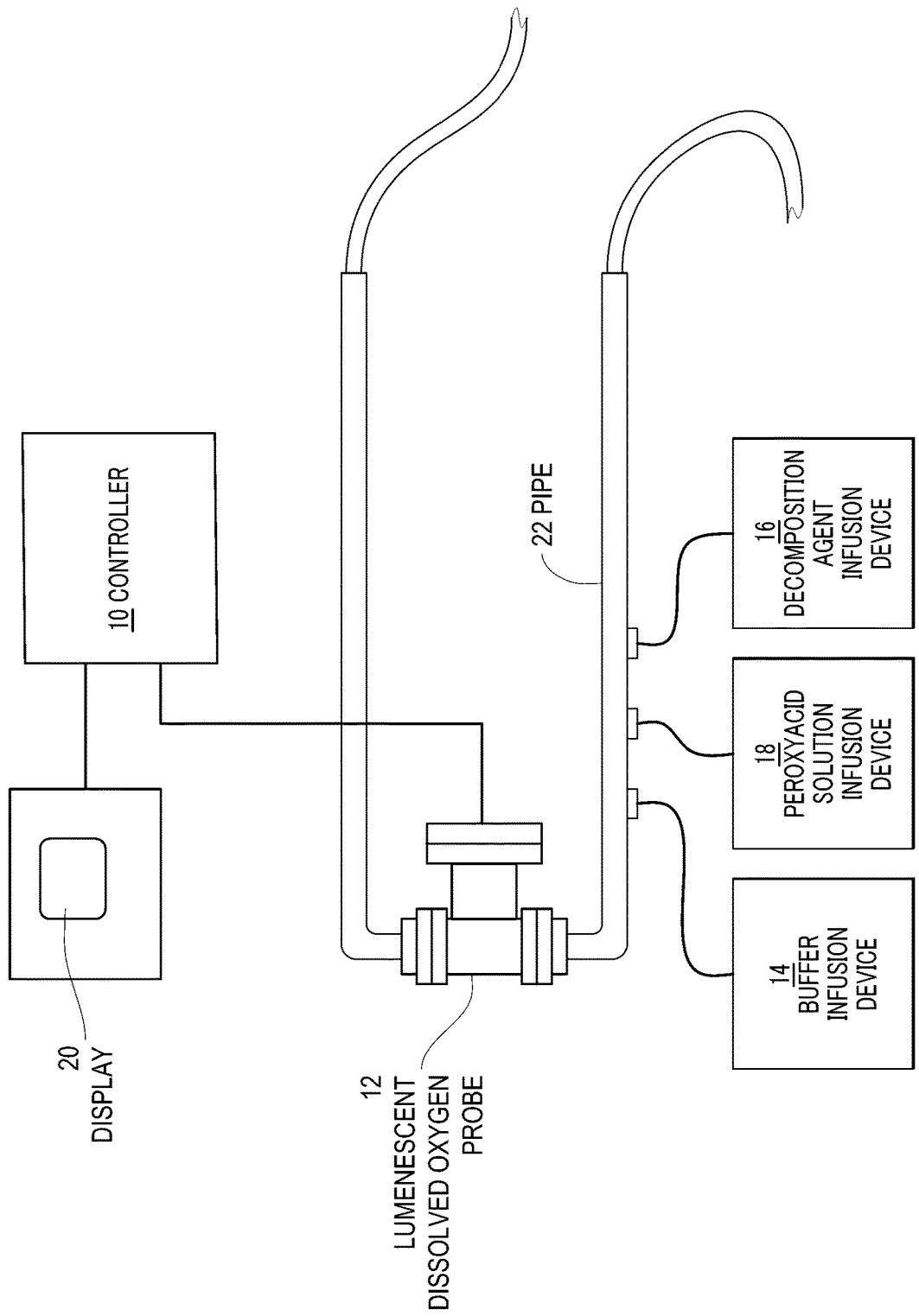
FIG. 5 is a schematic diagram illustrating an embodiment of a system including a controller and luminescent dissolved oxygen (LDO) probe for detecting and quantifying a peroxyacid by adding a decomposition agent and measuring the amount of dissolved oxygen.

FIG. 5 illustrates one embodiment of a system for analyzing and treating a fluid containing a peroxyacid or peroxide. The embodiment of FIG. 5 includes a controller 10, a display 20, a luminescent dissolved oxygen probe 12, a pipe 22, a buffer infusion device 14, a peroxyacid infusion device 18, and a decomposition agent infusion device 16. In the system shown in FIG. 5, fluid is diverted from a fluid stream or a sample of fluid is collected in the pipe 22. A buffer is introduced into the water via the buffer infusion device 14 to adjust the pH of the water in the pipe 22. Optionally, the dissolved oxygen probe 12 measures an initial amount of dissolved oxygen in the water. Then, a decomposition agent is introduced into the water via the decomposition agent infusion device 16. After waiting for a suitable amount of time for partial or total decomposition of the peroxyacid and/or peroxide to take place, the amount of dissolved oxygen in the water in the pipe 22 is measured by the dissolved oxygen probe 12.

Although the system illustrated in FIG. 5 uses a luminescent dissolved oxygen probe 12, the system may include any suitable sensor for directly or indirectly measuring a change in the amount of oxygen produced after the introduction of the decomposition agent, as discussed above. For example, the sensor may be any suitable sensor for measuring an amount of dissolved oxygen in the fluid. The sensor may also be any suitable sensor for measuring an amount of oxygen in a gaseous or liquid fluid. The sensor may also be any suitable sensor for measuring the pressure of a closed system containing the fluid.

The decomposition agent infusion device 16 can be configured to introduce any suitable decomposition agent into the fluid or sample thereof, including, for example, catalase enzyme, sodium hypochlorite (commonly known as bleach when dissolved in water), metal catalysts, alkaline solutions (such as sodium hydroxide), and haloamines. The decomposition agent infusion device 16 can also be configured to introduce a decomposition agent via a physical process, such as by irradiating the fluid or a sample thereof with ultraviolet (UV light).

The peroxyacid solution infusion device 18 in the system of FIG. 5 can be used to introduce known amounts of the peroxyacid and/or peroxide into the water sample in the pipe 22 for testing purposes to determine, for example, the standard curve representing the relationship between the amount of dissolved oxygen and the amount of peroxyacid or peroxide. For example, a known amount of peracetic acid may be introduced into the water via the peroxyacid solution infusion device 18 before the decomposition agent is introduced into the water via the decomposition agent infusion device 16 or before the buffer is introduced into the water via the buffer infusion device 14. The peroxyacid solution infusion device 18 may also be configured to introduce a predetermined amount of the peroxyacid solution into the fluid when it is determined that the amount of peroxyacid and/or peroxide in the fluid is below a threshold level. For example, the controller 10 may instruct the peroxyacid solution infusion device 18 to introduce a predetermined amount of the peroxyacid solution into the fluid when the controller determines that the amount of the peroxyacid and/or peroxide in the fluid is below a threshold amount based on the measured oxygen production in the fluid sample.

Although not illustrated in FIG. 5, the system may also include a neutralization agent infusion device for introducing an amount of a neutralization agent into the fluid stream, as discussed above. The neutralization agent infusion device can be configured to introduce any suitable decomposition agent into the fluid or sample thereof, including, for example, any decomposition agent or reducing agent. In one embodiment, the neutralization agent infusion device may be configured to divert the fluid steam to solid media containing a neutralization agent.

Each of the infusion devices can be any suitable device for introducing an accurate amount of the fluid, for example, the buffer, peroxyacid solution, decomposition agent, or neutralization agent into the fluid stream. For example, one or more of the infusion devices can be a pump connected to a container or reservoir that meters an accurate amount of the fluid, for example, the buffer, peroxyacid solution, or decomposition agent, or neutralization agent into the fluid stream via conduits and valves that can be controlled. Although the infusion devices have been described with respect to specific embodiment illustrated in FIG. 5, any suitable device capable of introducing the fluid to a decomposition agent, neutralization agent, buffer, peroxyacid solution, and/or any other suitable agent or substance and configurations thereof may be used.

The system illustrated in FIG. 5 also includes a controller 10, such as a processor or CPU. The controller 10 can control pump additions, timing, and recirculation, and can include memory for recording readings from the dissolved oxygen probe for determining the amount of peroxyacid or peroxide. In one aspect, the controller 10 can determine the amount of the peroxyacid or peroxide in the sample based on the measured amount of dissolved oxygen or the measured pressure after addition of the decomposition agent. For example, the controller 10 can determine the amount of the peroxyacid or peroxide based on an increase in the amount of the dissolved oxygen or the measured increase in pressure after the decomposition agent is introduced into the sample.

The controller 10 can also control the amount of the decomposition agent that is introduced into the sample and record the measured amount of dissolved oxygen and/or measured pressure in the memory for determining the amount of the peroxyacid or peroxide in the sample. The controller 10 can compare the measured increase in dissolved oxygen and/or measured pressure increase to a standard curve to determine the amount of peroxyacid and/or peroxide present in the fluid, and can send instructions for modifying the process conditions based on the calculated quantity, for example, adding more peroxyacid and/or peroxide, or adding a neutralization agent. The controller 10 can control an amount of the peroxyacid and/or peroxide that is added to the process based on the determined amount of peroxyacid or peroxide in the sample, and control an amount of a neutralizing agent that is added to the process based on the determined amount of the peroxyacid and/or peroxide. In this regard, the peroxyacid/peroxide solution can be kept in a container or tank and connected to the fluid system via a conduit with a valve that be controlled by instructions from the controller 10 to increase or decrease the concentration of peroxyacid/peroxide in the fluid. Similarly, the decomposition agent and neutralization agent can also be kept in containers or tanks connected to the fluid system via a conduit with a valve that can be controlled by instructions from the controller 10 to increase or decrease the concentration thereof in the fluid.

The system can also include a memory for storing data. For example, the standard curve and threshold amounts of the peroxyacid and/or peroxide can be stored in the memory. As mentioned above, the memory can also store the measured amounts of dissolved oxygen and/or measured pressure change for determining the amount of peroxyacid and/or peroxide in the sample. The memory can also store the determined amount of peroxyacid and/or peroxide. The memory may be in the form of any computer data storage, such as random-access memory or flash memory.

Systems that employ these methods can include a feedback control connected to the feed pump that introduces a peroxyacid disinfectant solution into the system. The feedback control loop can also be connected to a pump that introduces any neutralizing agent into the process stream to neutralize the peroxyacid and/or peroxide. The feedback control loop can also be connected to a valve or diverter that sends a portion of the process stream to a fixed media to remove or neutralize excess peroxyacid and/or peroxide.

Referring to FIG. 5, the system can employ a monitoring display 20 that shows the real-time amount of dissolved oxygen and the corresponding amount of the peroxyacid and/or peroxide, as well as the control steps that are being employed, e.g., the amount of neutralizing agent being added to the system, and any other information to the user. The display 20 may be, for example, a liquid crystal display (LCD) or any suitable display. The system can provide alerts (e.g., visual and/or audio alerts) if the system values deviate from expected or desired values, such as when the target peroxyacid and/or peroxide exceeds a threshold level in the system. In some processes, for example, the target peroxyacid and/or peroxide may only need to be neutralized by introducing a neutralizing agent into the fluid or directing the process stream to fixed media when the concentration exceeds a threshold value. The controller 10 may automatically instruct the neutralization agent infusion device to introduce the neutralization agent into the fluid or automatically direct the process to fixed media containing a neutralization agent when, for example, the target peroxyacid and/or peroxide values exceed threshold levels in the system. An operator may also manually adjust the amount of the neutralization agent, decomposition agent, and/or peroxyacid/peroxide solution being adding to fluid.

The controller 10 and/or display 20 may include navigational control pad including any input interface that allows a user to input commands and/or interact with the probe and/or controller 10. For example, the control pad may be in the form of a keypad. The control pad may, for example, allow an operator to enter variables, set parameters, access menu items, and the like. For example, the control pad may enable an operator to input threshold values of, for example, peroxyacid and/or peroxide concentrations and pH values.

For example, the controller 10 and/or display 20 may include inputs to control the oxygen probe, pressure sensor, and/or any other probe or sensor locally, or to locally control any other device that is connected to the controller 10. The controller 10 may also receive commands or other information from another controller or processor within a DCS to remotely control the oxygen probe, pressure sensor, and/or any other sensor or device connected thereto. For example, other devices, such as a buffer infusion device 14, a peroxyacid solution infusion device 18, a decomposition agent infusion device 16, or a neutralization agent infusion device (not shown) may also be (wired or wirelessly) connected to the controller 10.

The controller 10 may be connected to a wireless router and a distributed control system (DCS). The oxygen and/or pressure measurements may be sent to the controller from the dissolved oxygen probe 12, a pressure sensor (not shown), or any other oxygen sensor (for example, for measuring the amount of oxygen in the headspace in a closed system). These measurements and/or any other information may also be displayed on the display 20. The controller 10 may transmit the measurement and/or any other information via either a wired or wireless connection to another controller and/or processor within the DCS. For example, the information may be transmitted via wireless router. The controller 10 in FIG. 5 is a local controller. However, a remote or local controller and/or processor may receive the measurements from the probes and/or sensors, compare those measurements to a standard curve to determine the amount of the peroxyacid and/or peroxide in the fluid, and/or whether the determined amount is within prescribed limits. If the amount of the peroxyacid and/or peroxide is not within prescribed limits, the controller 10 or remote controller or processor, for example, within a DCS may send a command signal to the controller 10 to increase or decrease the amount of the peroxyacid and/or peroxide in the fluid. The controller 10 may cause the display 20 to display a warning to an operator that the amount of peroxyacid and/or peroxide is not within the prescribed limits. An operator can also manually adjust the amount of the peroxyacid and/or peroxide in the fluid.

The system can also include a refrigeration storage unit in which the decomposition agent can be stored. Storing, for example, the catalase enzyme in a refrigeration storage unit can help preserve enzyme efficiency.

In one embodiment, the system is configured to continuously monitor and control the peroxyacid and/or peroxide concentration in the fluid. For example, the system may be configured to measure the oxygen concentration and/or pressure following (and/or immediately before) the addition of the neutralization agent to continuously monitor the concentration of peroxyacid and/or peroxide in the fluid, and make the appropriate adjustments to the concentration as needed. For example, after the controller 10 determines the peroxyacid and/or peroxide concentration based on the measured values (e.g., the measured increase in oxygen or the measured increase in pressure), the controller 10 may instruct the peroxyacid solution infusion device 18 to introduce more of the peroxyacid solution into the fluid to increase the concentration of the peroxyacid and peroxide in the fluid if the controller determines the calculated concentration of the peroxyacid and/or peroxide is below the predetermined range. Alternatively, if the controller 10 determines that the peroxyacid and/or peroxide concentration is above the predetermined range based on the measured values, the controller 10 may instruct a neutralization infusion device to introduce a predetermined amount of the neutralization agent into the fluid to decrease the concentration of peroxyacid and peroxide in the fluid. Alternatively, the controller 10 may cause the fluid to be diverted to fixed media containing a neutralization agent to decrease the concentration of the peroxyacid and peroxide in the fluid. The peroxyacid and/or peroxide concentrations may be continuously measured until it is determined that the concentrations are within a predetermined range, and/or the peroxyacid and/or peroxide concentrations may be continuously measured at predetermined time intervals.

For example, the system may be configured such that the oxygen probe 12 measures the oxygen concentration or a pressure sensor measures pressure, and the decomposition agent infusion device 16 introduces a predetermined amount of the decomposition agent into the fluid or a sample thereof automatically at predetermined intervals. For example, the oxygen probe 12 or a pressure sensor may automatically measure an initial oxygen concentration or pressure, respectively, of the fluid or a sample thereof every 5 minutes, 15 minutes, 30 minutes, hour, 2 hours, or any other suitable interval. Then, the decomposition agent infusion device 16 could automatically introduce a predetermined amount of the decomposition agent into the fluid or a sample thereof. Then, after a predetermined period of time, the oxygen probe 12 or pressure sensor may automatically measure the oxygen concentration or pressure, respectively to determine the change in the oxygen concentration or pressure for the purpose of calculating the peroxyacid and/or peroxide concentration. For example, when the measurements are sent to the controller 10, the controller 10 may compare the measured values to a predetermined standard curve for determining the peroxyacid and/or peroxide concentration. Then, the controller 10 may instruct one or more of the infusion devices for adjusting the peroxyacid and/or peroxide concentration as needed to be within a predetermined range based on the calculated peroxyacid and/or peroxide concentration in the fluid.

The pH of the fluid may also be monitored and controlled to be within a desired range, as discussed above. For example, the pH may also be continuously measured at predetermined time intervals. Those measurements may be transmitted to the controller 10 for comparing to a predetermined pH range. If the controller 10 determines that the measured pH is outside of the predetermined range, then the controller may instruct the buffer infusion device 14 to introduce a buffer into the fluid for adjusting the pH of the fluid to within the predetermined range. The pH may be continuously measured and sent to the controller until the pH is determined to be within the predetermined range or until a predetermined time interval has passed.

The present methods and systems offer several advantages over existing methods and systems. The methods and systems, as well as their advantages, will be described in greater detail by way of specific examples.

EXAMPLES

The following examples are offered for illustrative purposes, and are not intended to limit nor define the invention in any manner.

Example 1

Known amounts of a peracetic acid/hydrogen peroxide product, which has a 50:50 ratio of peracetic acid to hydrogen peroxide, were added to fluid samples (250 ml) collected in a pipe. A buffer was added to each sample to adjust the pH of the sample to about 7. An initial concentration of dissolved oxygen in each sample was measured using a Hach LDO® luminescent dissolved oxygen probe. Then, a catalase enzyme was added to each sample at a concentration of 2.5 mg/L and the pipe was closed. However, the pipe or other vessel containing the sample does not have to be closed. After about 5 minutes, the Hach LDO® luminescent dissolved oxygen probe was used to measure the dissolved oxygen levels. The increases in the dissolved oxygen levels was then plotted against the known peroxide concentrations for the samples, and a regression of these data points was performed to produce the standard curve shown in FIG. 1. The graph in FIG. 1 shows that the amount of dissolved oxygen that is produced after the addition of the catalase enzyme (on the y-axis) is substantially proportional to the amount of active peracetic acid (on the x-axis) present in the samples. The x-axis numbers represent only the peracetic acid amounts in the samples. In particular, FIG. 1 shows a substantially linear relationship with an $r^2$ value of about 0.97 between the dissolved oxygen concentration and the active peracetic acid concentration in the presence of a catalase enzyme. Because the catalase enzyme only breaks down hydrogen peroxide, the amount of dissolved oxygen that is produced will be directly proportional to the amount of hydrogen peroxide present in the sample.

Example 2

Samples containing deionized water buffered at 9.3 with borax, and known amounts of peracetic acid were collected in a pipe. An initial concentration of dissolved oxygen in each sample was measured using a Hach LDO® luminescent dissolved oxygen probe. Then, sodium hypochlorite (NaOCl) at an active concentration of 50 ppm was added to each sample and the pipe was closed. The Hach LDO® luminescent dissolved oxygen probe was used to measure the dissolved oxygen levels at 1 minute after the addition of sodium hypochlorite and after completion of the decomposition reaction. The standard curves of FIG. 3 were produced by plotting the increases in the dissolved oxygen levels at 1 minute (bottom curve) after addition of sodium hypochlorite and after completion of the decomposition reaction (top curve) against the known peroxide concentrations for the samples, and a regression of these data points was performed. As shown by the bottom curve with square points in FIG. 3, the amount of dissolved oxygen that is produced one minute after the addition of the sodium hypochlorite (on the y-axis) is substantially proportional to the amount of peracetic acid (on the x-axis) present in the samples. As shown by the top curve diamond points in FIG. 3, the amount of dissolved oxygen that is produced after completion of the decomposition reaction (on the y-axis) is also substantially proportional to the amount of peracetic acid (on the x-axis) present in the samples.

Therefore, FIG. 3 shows a substantially linear relationship between the dissolved oxygen concentration and the peracetic acid concentration in the presence of a sodium hypochlorite (NaOCl) one minute into the decomposition reaction and after completion of the decomposition reaction (i.e., after the peracetic acid is completely consumed).

Example 3

Three fluid samples containing peracetic acid were prepared for determining the rates of dissolved oxygen production (1) in the presence of catalase as the decomposition agent; (2) in the presence of UV light as the decomposition agent; and (3) in the absence of a decomposition agent at a pH of 7.11 (i.e., the natural decomposition of peracetic acid). A dissolved oxygen sensor was used to measure the change in dissolved oxygen concentration over time. In sample (1), catalase was added as the decomposition agent at about 900 seconds. Similarly, in sample (2) UV light was irradiated into the sample starting at about 900 seconds. In sample (3), no decomposition agent was added to the sample.

FIG. 4 is a graph showing the rates of dissolved oxygen production in the three fluid samples. As shown in FIG. 4, there is a sharp increase in the dissolved oxygen concentration starting about 900 seconds when the catalase enzyme was added in sample (1). There is also an increase in the dissolved oxygen concentration starting at about 900 seconds when UV light is irradiated onto sample (2). However, as shown in FIG. 4, the rate of dissolved oxygen production when UV light is used as the decomposition agent in sample (2) is lower than that when catalase enzyme is used as the decomposition agent in sample (1). When no decomposition agent is used (at a pH of 7.11) in sample (3), the dissolved oxygen concentration increases linearly over time at a rate lower than that when catalase (sample (1)) and UV light (sample (2)) are used as the decomposition agents. The natural decomposition rate of peracetic acid is lower than that when catalase and UV light are used as the decomposition agents.

Example 4

Figure 6:
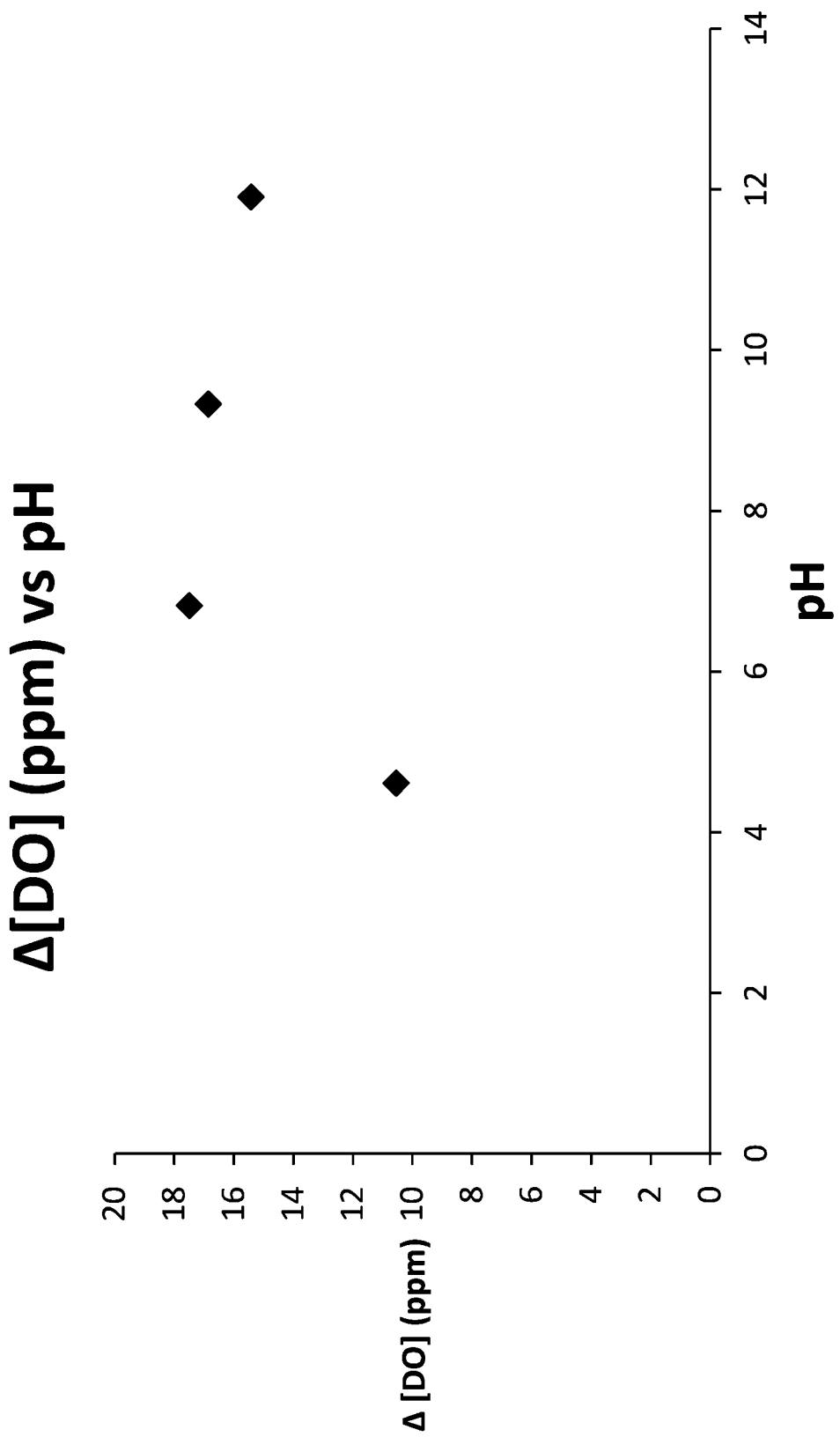
FIG. 6 is a graph showing the effect of pH on the change in the amount of dissolved oxygen produced by the reaction of peracetic acid and a decomposition agent.

The effect of pH on the reaction between the decomposition agent and paracetic acid was tested. Four samples of water each containing the same amount of paracetic acid. In particular, the peracetic acid concentration in each of the four samples was 15 ppm were prepared. The samples were buffered to various pH values. A decomposition agent was introduced into each of the samples at an active concentration of 50 ppm. Then, the change in the dissolved oxygen concentration in each of the samples was measured. As shown in FIG. 6, the amounts of dissolved oxygen production were about the same in the samples having a pH of about 6.5 or higher. Although there is a slight decrease in the measured dissolved oxygen production at a pH of 11.91, this is likely due to peracetic acid breaking down on its own at a high pH. However, at a lower pH of about 4, the change in the amount of dissolved oxygen was less reproducible.

Example 5

The amount of peracetic acid in a process stream was periodically monitored over time via a peracetic acid monitoring test unit. The unit was programmed to take a fluid sample, introduce a decomposition agent into the fluid sample, measure the change in the dissolved oxygen amount in the sample after the introduction of the decomposition agent, and determine the amount of peracetic acid in the fluid based on the measured change in the dissolved oxygen amount. The unit was programmed to perform these steps once every 30 minutes.

Figure 7:
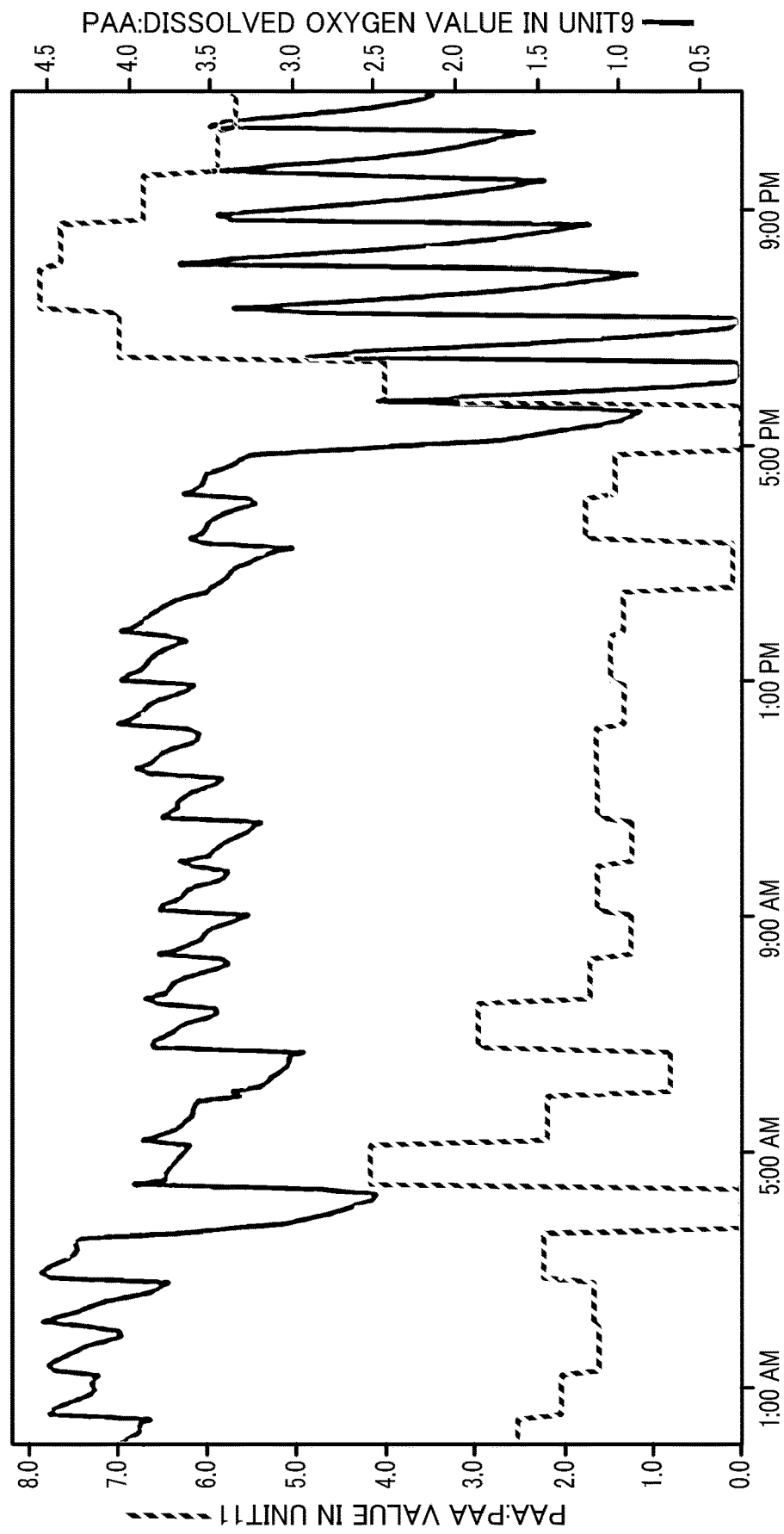
FIG. 7 is a graph showing the results of monitoring the amount of peracetic acid in a process stream by calculating the amount peracetic acid (left y-axis) once every thirty minutes based on the change in dissolved oxygen levels (right y-axis).

The results are shown in FIG. 7. In the graph shown in FIG. 7, the right side y-axis shows the dissolved oxygen levels, and the left side y-axis shows the peracetic acid concentration. The top curve at least at the left-hand side represents the change in dissolved oxygen amounts, and the bottom curve represents the calculated peracetic acid concentrations. As shown in FIG. 7, the amount of peracetic acid and/or peroxide can be monitored and controlled by periodically analyzing a fluid sample for calculating the peroxyacid and/or peroxide concentration in the fluid, and adjusting the peroxyacid and/or peroxide concentration in the fluid based on the calculated values to be within a predetermined range.

It will be appreciated that the above-disclosed embodiments, features, and functions, or alternatives thereof, may be desirably combined into different systems or methods. Also, various alternatives, modifications, variations or improvements may be subsequently made by those skilled in the art, and are also intended to be encompassed by the following claims. As such, various changes may be made without departing from the spirit and scope of this disclosure as defined in the claims.

What is claimed is:

1. A method of analyzing a fluid that includes at least one of peroxyacid and peroxide, the method comprising:
   introducing into the fluid a decomposition agent that decomposes the peroxyacid and/or peroxide into decomposition products;
   directly measuring an amount of dissolved oxygen that is produced in the fluid as one of the decomposition products resulting from the decomposition of the peroxyacid and/or peroxide by the decomposition agent; and
   then determining an amount of the peroxyacid present in the fluid based on the measured amount of the dissolved oxygen.

2. The method according to claim 1, further comprising directly measuring an amount of dissolved oxygen in the fluid before introducing the decomposition agent into the fluid.

3. The method according to claim 1, wherein the fluid has been treated such that it is substantially free of peroxide and is in a gaseous phase before the introduction of the decomposition agent.

4. The method according to claim 3, wherein, in the measuring step, the amount of the dissolved oxygen is directly measured in the gaseous fluid.

5. The method according to claim 1, wherein the peroxyacid is peracetic acid.

6. The method according to claim 1, wherein the decomposition agent is selected from the group consisting of catalase, sodium hypochlorite, metal catalyst, alkaline solution, haloamine, and ultraviolet light.

7. The method according to claim 1, further comprising adjusting the pH of the fluid to be in a range of from 6.5 to 11.5.

8. The method according to claim 1, wherein the measuring step is performed after partial decomposition of the peroxyacid and/or peroxide in the fluid.

9. A method of monitoring and controlling an amount of peroxyacid in a fluid, the method comprising:
    introducing into a sample of the fluid a decomposition agent that decomposes the peroxyacid and/or peroxide into decomposition products;
    directly measuring an amount of dissolved oxygen that is produced in the fluid as one of the decomposition products resulting from the decomposition of the peroxyacid and/or peroxide by the decomposition agent;
    then determining an amount of the peroxyacid present in the fluid based on the measured amount of the dissolved oxygen; and
    adjusting the amount of the peroxyacid in the fluid based on the determined amount thereof.

10. The method according to claim 9, wherein, in the adjusting step, the amount of the peroxyacid in the fluid is adjusted to be within a predetermined range.

11. The method according to claim 9, wherein, in the adjusting step, the amount of the peroxyacid in the fluid is adjusted by:
    adding more of the peroxyacid into the fluid to increase the amount thereof in the fluid, or
    introducing a neutralization agent into the fluid to decrease the amount of the peroxyacid in the fluid.

12. The method according to claim 11, wherein the neutralizing agent is selected from the group consisting of bisulfite, erythorbate, cerium (III), catalase, sodium hypochlorite, metal catalyst, alkaline solution, haloamine, and ultraviolet light.

13. A system for analyzing and treating a fluid containing at least one of peroxyacid and peroxide, the system comprising:
    a sample collector configured to collect a sample of the fluid;
    a decomposition agent infusion device configured to introduce into the sample a decomposition agent that decomposes the peroxyacid and/or peroxide into decomposition products;
    a sensor configured to directly measure an amount of dissolved oxygen that is produced in the fluid as one of the decomposition products resulting from the decomposition of the peroxyacid and/or peroxide by the decomposition agent; and
    a controller configured to determine an amount of the peroxyacid in the fluid based on the measured amount of the dissolved oxygen by the sensor.

14. The system according to claim 13, wherein the controller is further configured to control the amount of peroxyacid, or an amount of a neutralization agent that is introduced into the fluid based on the determined amount of the peroxyacid in the fluid.

15. The system according to claim 13, further comprising a neutralization agent infusion device configured to introduce a neutralization agent into the fluid.

16. The method according to claim 1, wherein:
    the decomposition agent decomposes peroxide and not peroxyacid; and
    the amount of peroxyacid is determined based on the measured amount of the dissolved oxygen produced from the decomposition of peroxide.

17. The method according to claim 1, wherein the amount of the dissolved oxygen is directly measured by a sensor.

* * * * *